(12) United States Patent
Tsuboi et al.

(10) Patent No.: US 6,289,250 B1
(45) Date of Patent: Sep. 11, 2001

(54) IMPLANTABLE ELECTRODE LEAD

(75) Inventors: Fuminori Tsuboi; Katsuhiro Shirakawa; Kunimasa Katayama, all of Nakai-machi (JP)

(73) Assignee: Kabushiki Kaisha Cardio-Pacing Research Laboratory, Kanagawa-Ken (JP)

(*) Notice: Subject to any disclaimer, the term of this patent is extended or adjusted under 35 U.S.C. 154(b) by 0 days.

(21) Appl. No.: 09/380,464
(22) PCT Filed: May 26, 1999
(86) PCT No.: PCT/JP99/02762
 § 371 Date: Sep. 3, 1999
 § 102(e) Date: Sep. 3, 1999
(87) PCT Pub. No.: WO99/61098
 PCT Pub. Date: Dec. 2, 1999

(30) Foreign Application Priority Data

May 27, 1998 (JP) .................................................. 10-146279

(51) Int. Cl.[7] .................................................. A61N 1/05
(52) U.S. Cl. ............................................. 607/122; 600/374
(58) Field of Search ................................. 607/119, 122, 607/123, 121; 600/373–381

(56) References Cited

U.S. PATENT DOCUMENTS

| | | |
|---|---|---|
| 4,840,186 | 6/1989 | Lekholm et al. . |
| 5,318,572 | 6/1994 | Helland et al. . |
| 5,796,044 | * 8/1998 | Cobian et al. ........................ 607/119 |

FOREIGN PATENT DOCUMENTS

| | | |
|---|---|---|
| 56-33943 | 8/1979 | (JP) . |
| 58-192206 | 11/1983 | (JP) . |
| 64-11563 | 1/1989 | (JP) . |
| 6-261953 | 9/1994 | (JP) . |

* cited by examiner

Primary Examiner—Jeffrey R. Jastrzab
(74) Attorney, Agent, or Firm—Burns, Doane, Swecker & Mathis, LLP

(57) ABSTRACT

In order to increase durability against repeated flexure caused in a body tissue or flexure having a very small radius of curvature, and to reduce mechanical stress applied by a lead body on the body tissue, a lead body (20) of an implantable electrode lead is constituted by a conductive coil (24) and a sheath (22). The conductive coil (24) is obtained by helically winding a conductive wire (26), formed with an insulating coating layer (28) and having a diameter (d), to have a coil pitch diameter (mean diameter) (D). The sheath (22) is made of an electrical insulating material. An outer diameter G of the lead body (20) is set to 2 mm or less. The sheath (22) is formed of a soft material having a Shore hardness of 80A or less. The conductive coil (24) is set to have a spring index (D/d) of 7.8 or more.

6 Claims, 5 Drawing Sheets

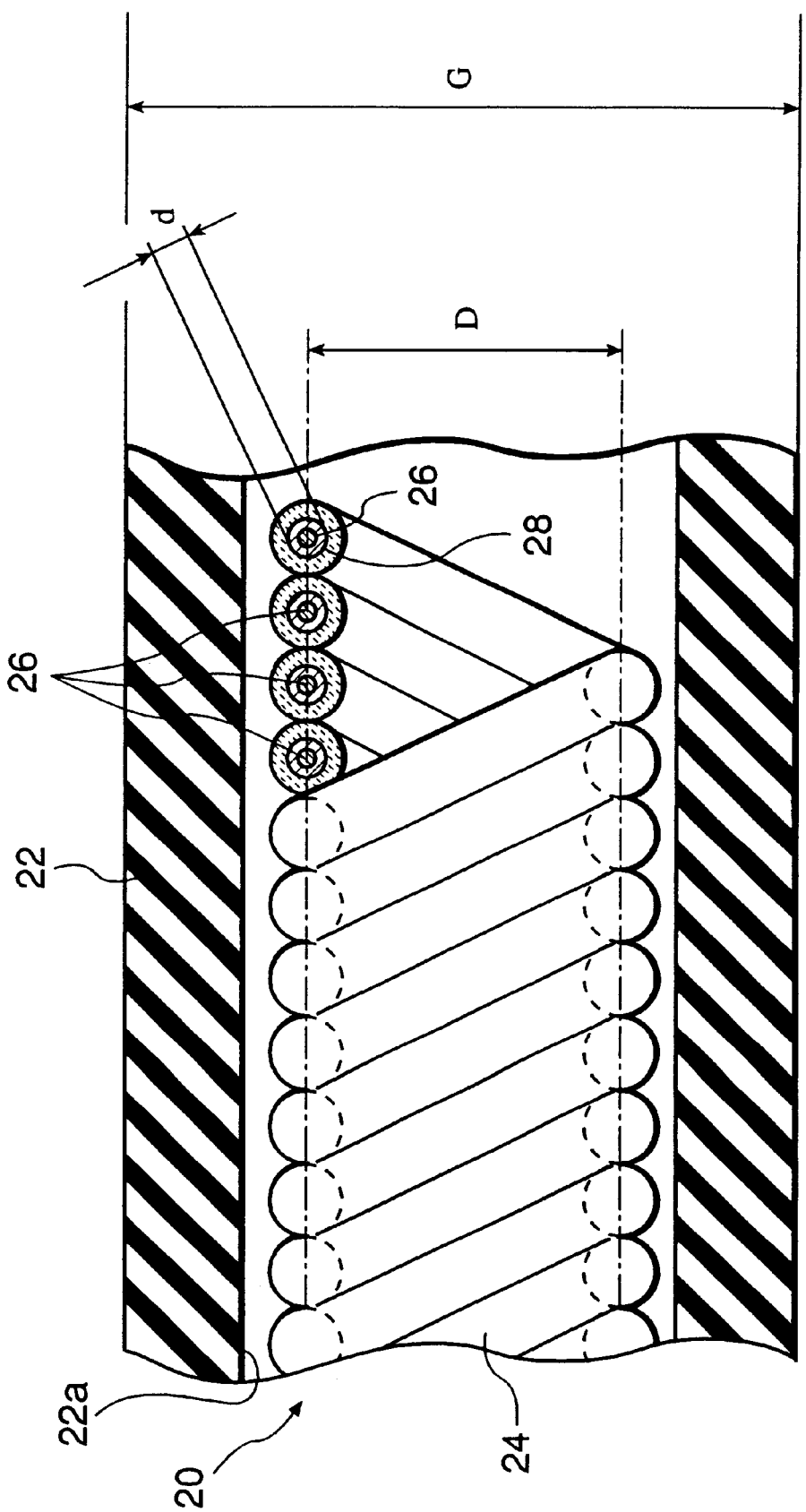

FIG. 6

| | $<10^6$ | $10^6 \sim 10^7$ | NUMBER OF TIMES OF FLEXURE $10^7 \sim 10^8$ | $>10^8$ |
|---|---|---|---|---|
| T1 (n=5) | — | — | 1 | 4 |
| T2 (n=5) | — | — | — | 5 |
| T3 (n=5) | — | — | — | 5 |
| S1 (n=5) | 5 | — | — | — |
| S2 (n=5) | 3 | 1 | 1 | — |
| S3 (n=3) | — | 2 | 1 | — |
| S4 (n=3) | 3 | — | — | — |

IMPLANTABLE ELECTRODE LEAD

BACKGROUND OF THE INVENTION

1. Field of the Invention

The present invention relates to an implantable electrode lead and, more particularly, to an implantable electrode lead to be implanted in body tissue, which improves the repetition durability of the lead body of the electrode lead in the body tissue when used generally together with a cardiac pacemaker or implantable defibrillator and which can reduce the mechanical stress applied by the lead body onto the body tissue because of its softness.

2. Description of the Related Art

Many types of implantable electrode leads used together with a cardiac pacemaker or implantable defibrillator are conventionally known. Generally, an electrode lead is constituted by at least one electrode, an electrical connector, and a lead body, and is used as an implantable electrode lead. The electrode electrically stimulates the heart or senses electrical cardiac activity in one or both of the chambers of the heart. The electrode lead is electrically connected to the cardiac pacemaker or implantable defibrillator through the electrical connector. The lead body is arranged between the electrode and electrical connector, and is formed of an electrical conductor and a bio-compatible electrically insulating cover. The electrical conductor transmits an electrical signal between the electrode and the cardiac pacemaker or implantable defibrillator.

In a transvenously used implantable electrode lead, the electrode and part of the lead body are inserted in the heart and vein. The lead body outside the vein and the electrical connector are extended to a connection housing for the cardiac pacemaker or defibrillator and connected to it.

Currently, in the lead body of a bipolar implantable electrode lead, a coaxial structure constituted by two types of conductive coils having different pitch diameters (mean diameters), an insulating sheath located between the two conductive coils, and a sheath located on the outermost surface of the lead body is the main stream.

According to another lead structure, a sheath is formed on the outer surface of an insulating parallel-wound coil on which a conductive wire with insulating coating is wound with the same pitch diameter (mean diameter).

Generally, in a conductive coil used in an implantable electrode lead, since the conductive wire is helically wound, when the lead body deforms, the internal stress of the conductive wire is reduced. It is known that the larger the spring index (D/d), the larger this internal stress reducing effect where D is the pitch diameter (mean diameter) of the conductive coil, d is the diameter of the conductive wire, and d and D are constant.

SUMMARY OF THE INVENTION

An implantable electrode lead inserted by puncture reaches the heart chamber through the subclavian vein. Since it is repeatedly pressed by the clavicle and the first rib, the electrode lead sometimes fractures to pose a clinical problem. Attempts have been made to solve this problem in terms of implantation by performing puncture at an appropriate portion where the electrode lead will not be easily damaged. If, however, the electrode lead has a large outer diameter, not only the load on the electrode lead applied by the clavicle and first rib increases, but also the electrode lead is difficult to be inserted in the blood vessel. It is also pointed out that when a plurality of leads are to be inserted in the cardiac ventricle, tricuspid incompetence can be caused.

Improvement is accordingly made to decrease the outer diameter of the electrode lead. In the conventional coaxial structure, it is difficult to further decrease the outer diameter of the lead due to its structure. In particular, when silicone is used as the sheath material, since its mechanical characteristics, e.g., the tearing strength, are generally inferior to those of polyurethane, the sheath must have a large thickness, resulting in a large electrode lead diameter. When the number of stimulations to be transmitted to the lead body or the number of signals to be sensed is to be increased, the conductive coil must be extended in the radial direction of the lead body, thus increasing the outer diameter of the electrode lead.

In the bipolar electrode lead, when the lead body undergoes a pressure load, the insulating sheath located between the two conductive coils may be damaged to cause an insulation failure, which is a clinical problem.

With the structure in which the sheath is formed on the outer surface of the parallel-wound conductive wire on which the conductive wire with an electrically insulating coating layer is formed to have the same pitch diameter (mean diameter), the number of stimulations to be transmitted to the lead body or the number of signals to be sensed can be increased easily by increasing the number of coils without increasing the outer diameter of the lead, which is advantageous.

Even in the electrode lead having an increased number of coils, when a polyurethane material having comparatively high hardness (Shore hardness: 55D) is used as the sheath material, the sheath is permanently deformed or buckled when it is subjected to repeated flexure or flexure with a very small radius of curvature. An excessive load acts on the conductive coil to likely disconnect it. Since the pitch of the conductive coil is increased in accordance with the thickness of the insulating coating layer, a decrease in flexure durability may degrade. Conventionally, these problems have been coped with by minimizing the number of conductive wires assigned to transmit one electrical signal or increasing the pitch diameter (mean diameter) of the conductive coils.

However, these countermeasures are not effective at all in terms of failsafe measure against disconnection and further decrease in the outer diameter of the electrode lead. Therefore, improvement has been sought for.

The present invention has been made in view of the problems described above, and has as its object to provide an implantable electrode lead in which durability against the pressure applied under the clavicle, repeated flexure caused in the body tissue, or flexure with a very small radius of curvature is improved, and the lead body of which has softness to reduce the mechanical stress applied by the lead body on the body tissue.

In order to solve the above problems and to achieve the above object, the present invention relates to a small-diameter lead having excellent flexure durability, and provides a combination of the preferable mechanical characteristics of the conductive coil and sheath. More specifically, according to the present invention, there is provided an implantable electrode lead having connecting means arranged at a proximal end of a lead body and mechanically and electrically connected to an implantable device, and at least one electrode arranged at a distal end of the lead body in order to transmit an electrical signal between the implantable device and the electrode which is implanted in a predetermined portion to perform one or both of transmission of electrical stimulation to body tissue and sensing of an electrical signal from the body tissue, characterized in that the lead body is constituted by a conductive coil obtained by helically winding a conductive wire formed with an insulating coating layer and having a diameter (d) to have a coil pitch diameter (mean diameter) (D), and a sheath made of a bio-compatible electrically insulating material to cover an outer surface of the conductive coil, and the lead body is set to have an outer diameter of not more than 2 mm, the electrically insulating material of the sheath is formed of a soft material having a Shore hardness of less than 80A, and the conductive coil is set to have a spring index (D/d) of larger than 7.8.

The implantable electrode lead is characterized in that the conductive coil is formed by a multi-filar structure obtained by winding a plurality of conductive wires to have the same coil pitch diameter (D). The implantable electrode lead is characterized in that the electrode comprises a plurality of electrodes so that one of the conductive wires transmit one electrical signal while remaining ones of the conductive wires transmit other electrical signals.

The implantable electrode lead is characterized in that the conductive wire comprises a plurality of conductive wires to transmit one electrical signal, so that even if one conductive wire is disconnected, the electrical signal can be transmitted by the remaining conductive wires.

The implantable electrode lead is characterized in that the insulating coating layer of the conductive coil is formed of a fluoroplastic material.

The implantable electrode lead is characterized in that a difference in size between an outer circumference of the conductive wire and an inner circumference of the sheath is set to not less than 50 $\mu$m.

The implantable electrode lead is characterized in that the conductive wire is formed of a first metal material having a low electric resistivity and a second metal material having excellent corrosion resistance and mechanical characteristics to form a composite structure or cladding structure.

The implantable electrode lead is characterized in that a material having an electric resistivity of not more than 5.0 $\mu\Omega\cdot$cm at room temperature of 20° C. is used as the first metal material.

The implantable electrode lead is characterized in that the first metal material is silver.

When the above arrangement is employed, durability against the pressure applied under the clavicle, repeated flexure caused in the body tissue, or flexure with a very small radius of curvature is improved. Since the lead body has softness, the mechanical stress applied by the lead body on the body tissue is reduced.

BRIEF DESCRIPTION OF THE DRAWINGS

FIG. 2 is a sectional view taken along the line of arrows A—A of FIG. 1,

FIG. 6 is a table showing the results of the flexure test in FIG. 4.

DETAILED DESCRIPTION OF THE PREFERRED EMBODIMENT

One embodiment of the present invention will be described in detail with reference to the accompanying drawings.

Figure 1:
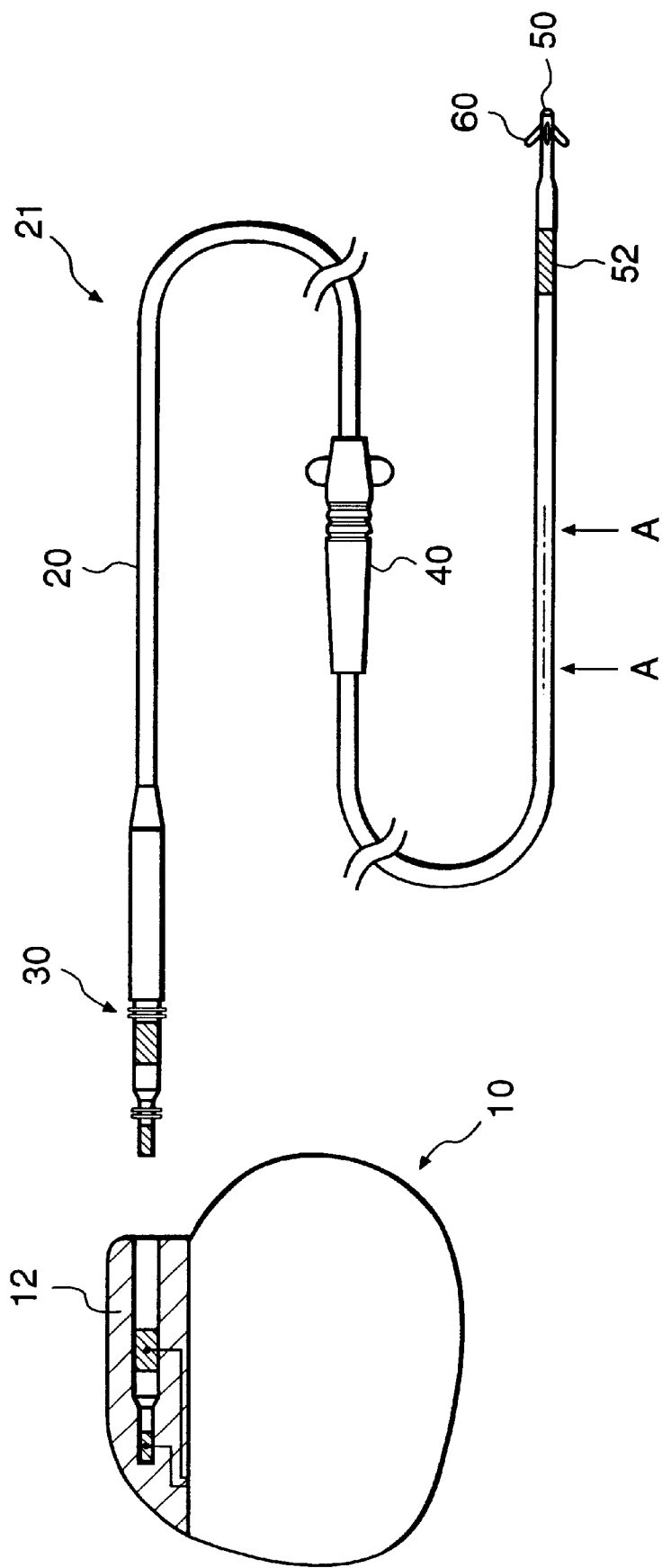
FIG. 1 is a view showing the outer appearance of an implantable electrode lead.

FIG. 1 is a view showing the outer appearance of a pacemaker and an implantable electrode lead. Referring to FIG. 1, an implantable electrode lead 21 has a flexible, predetermined-length lead body 20 having implantable electrodes 50 and 52 at its distal end and on its outer circumferential surface, respectively, and a connector 30 at the proximal end. The connector 30 is mechanically and electrically connected to a connector cavity 12 of a cardiac pacemaker 10 or an implantable defibrillator (not shown) to be detachable. The structure for electrical insulation and sealing of this mechanical and electrical connection is shown in FIG. 1, and a detailed description of this structure will be omitted. An endocardium fixing portion 60 is formed near the implantable electrode 50. The endocardium fixing portion 60 has a shaped portion (shown) which is to be hung from the trabeculae carneae or chordae tendineae in the heart chamber to fix the implantable electrode 50 to the endocardium immobile.

A sleeve 40 is mounted on the outer surface of the lead body 20 to be movable along the longitudinal direction of the lead body 20. When fixing the implantable electrode lead 21 with the body tissue near its portion to be inserted into the vein, the sleeve 40 protects the lead body 20. The lead body 20 and the body tissue are fixed to each other by stitching the outer surface of the sleeve 40 together with the lead body 20.

Subsequently, the lead body 20 will be described with reference to FIG. 2 as a sectional view taken along the line of arrows A—A of FIG. 1. In order to reduce the pressure repeatedly applied on the implantable electrode lead 21 by the clavicle and the first rib, the lead body 20 preferably has an outer diameter G of 2 mm or less. An electrical conductive coil 24 of the lead body 20 preferably has an insulated multi-filar structure which is advantageous in coping with a multi-polar electrode wire and in realizing a small-diameter lead. A single-filar structure is also acceptable, as a matter of course.

Generally, the total length of the implantable electrode lead 21 falls within a range of 400 mm to 600 mm. Therefore, after the conductive coil 24 is formed, the step of applying a sheath 22 on the sheath 22 is employed. During this step, a permanent forming strain sometimes remains between the conductive coil 24 and sheath 22. In order to reduce permanent forming strain residue, the difference in size between the outer circumferential surface of the conductive coil 24 and an inner-diameter portion 22a of the sheath 22 is preferably set to 50 $\mu$m (0.05 mm) or more. If the difference (clearance) in size between the outer circumferential surface of the conductive coil 24 and the inner-diameter portion 22a of the sheath 22 is set to 50 $\mu$m or more in this manner, when a flexure load is applied to the lead body 20, the mutually acting forces of the sheath 22 and conductive coil 24 can be reduced, so that the service life of the lead body 20 against flexure can be prolonged.

A conductive wire 26 constituting the electrical conductive coil 24 is formed with an insulating coating layer 28. When the lead body 20 is subjected to a repeated flexure load, the slidable contact between the sheath 22 and the insulating coating layer 28 of the electrical conductive coil 24 increases. If the clearance as described above is provided, this slidable contact can be reduced, and the service life of the lead body 20 against flexure can be prolonged.

Figure 3A:
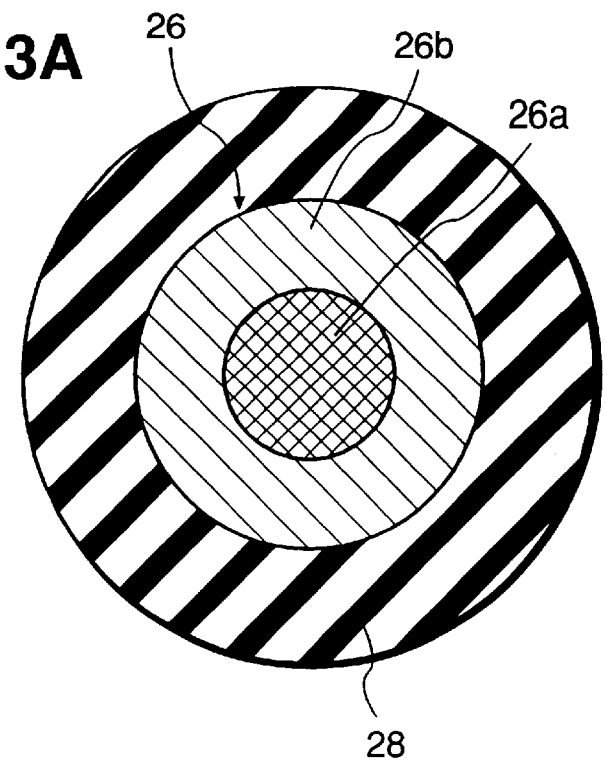
FIGS. 3A and 3B are sectional views of a conductive wire.
Figure 3B:
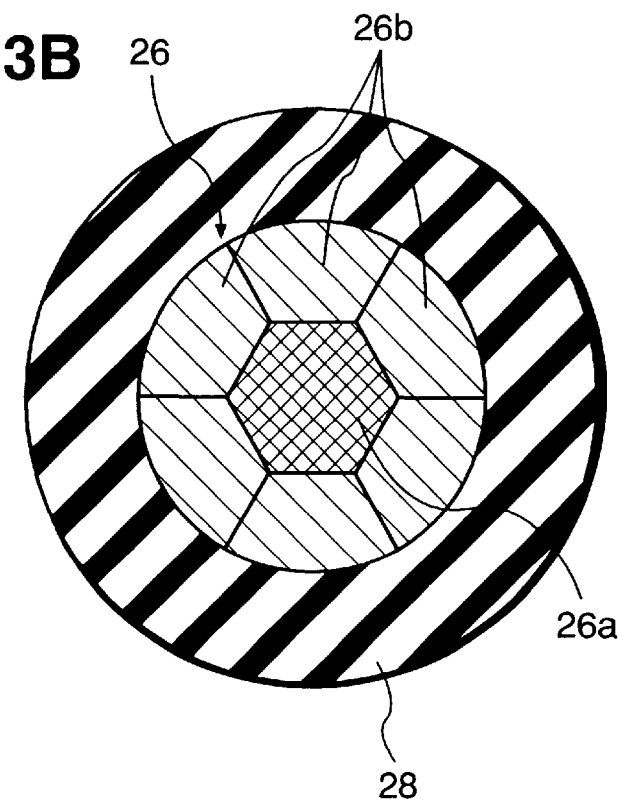

In the cross-sectional view of the conductive wire 26 of each of FIGS. 3A and 3B, if the conductive wire 26 uses a composite structure constituted by a first metal material 26a, e.g., silver or copper, having a low electric resistivity, and a second metal material 26b, e.g., stainless steel or cobalt-based alloy, having excellent corrosion resistance and mechanical characteristics, the pacing energy can be economized. The electric resistivity of the first metal material 26a is preferably 5.0 μΩ·cm or less at room temperature of 20° C., and silver having an electric resistivity of 1.59 μΩ·cm at room temperature of 20° C. is preferably used. As the typical examples of the conductive wire 26, DFT (Drawn Filled Tubing) shown in FIG. 3A and DBS (Drawn Brazed Strand) shown in FIG. 3B are available. According to DFT, in the cross section of the conductive wire 26, the core is made of the first metal material 26a, and the remaining peripheral portion is made of the second metal material 26b. According to DBS, in the cross section of the conductive wire 26, the core and the boundary portion are made of the first metal material 26a, and the partitioned elements located on the periphery of the core are made of the second metal material 26b.

The respective examples of the present invention will be described with reference to FIG. 2.

EXAMPLE 1

A lead body 20 of Example 1 (T1) has an outer diameter G of 1.9 mm. The material of a sheath 22 is silicone having a Shore hardness of 70A.

An electrical conductive coil 24 is formed of a multi-filar structure of four conductive coils 24 each formed with an insulating coating layer 28 made of a fluoroplastic. A spring index (D/d) as a ratio of the coil pitch diameter (mean diameter) (D) of the electrical conductive coil 24 to the diameter (d) of the conductive wire 26 is 9.0.

Of the conductive wire 26, the sectional area of the first metal material 26a occupies 25% the entire sectional area, and silver is used to form the first metal material 26a. To form the remaining portion of the conductive wire 26, the DFT wire (described above) formed of the cobalt-based alloy as the second metal material 26b is used.

EXAMPLE 2

Example 2 (T2) is obtained by replacing the material of the sheath 22 of Example 1 (T1) with silicone having a Shore hardness of 55A.

EXAMPLE 3

Example 3 (T3) is obtained by changing the spring index of the electrical conductive coil 24 of Example 1 (T1) to 10.0.

Comparative Example 1

Comparative Example 1 (S1) is obtained by changing the spring index of the electrical conductive coil 24 of Example 1 (T1) to 6.3.

Comparative Example 2

Comparative Example 2 (S2) is obtained by changing the spring index of the electrical conductive coil 24 of Example 1 (T1) to 7.8.

Comparative Example 3

Comparative Example 3 (S3) is obtained by replacing the material of the sheath 22 of Example 1 (T1) with silicone having a Shore hardness of 80A.

Comparative Example 4

Comparative Example 4 (S4), the material of the sheath 22 of Example 1 is replaced with polyurethane having a Shore hardness of 55D. The outer diameter of a lead body 20 is 1.5 mm. An electrical conductive coil 24 is constituted by two conductive wires 26 each formed with an insulating coating layer 28 made of a fluoroplastic. The spring index (D/d) of the electrical conductive coil 24 and conductive wires 26 is 6.36.

Figure 5:
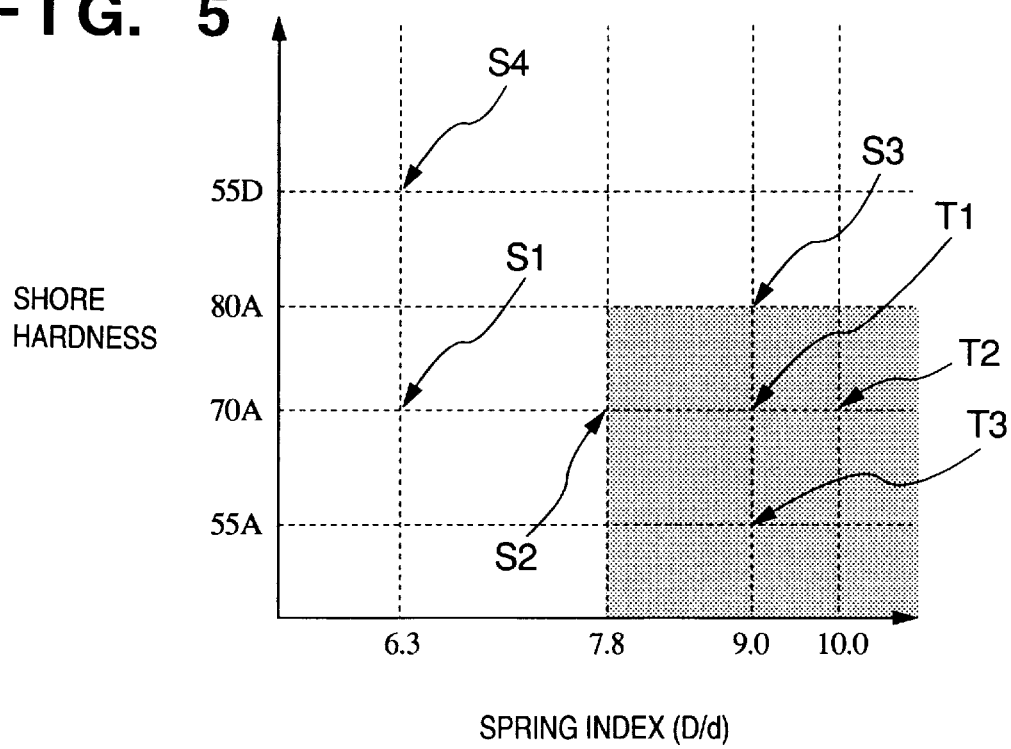
FIG. 5 is a graph showing the relationship between the hardness of the sheath material and the spring index of the electrical conductive coil of the examples and the comparative examples.

In FIG. 5, Examples 1 to 3 and Comparative Examples 1 to 4 are plotted in the graph defined by the hardness and spring index. The hatched portion in FIG. 5 includes Examples 1 to 3 described above. A lead body 20 constituted by a combination in this hatched region exhibited good flexure durability.

Figure 4:
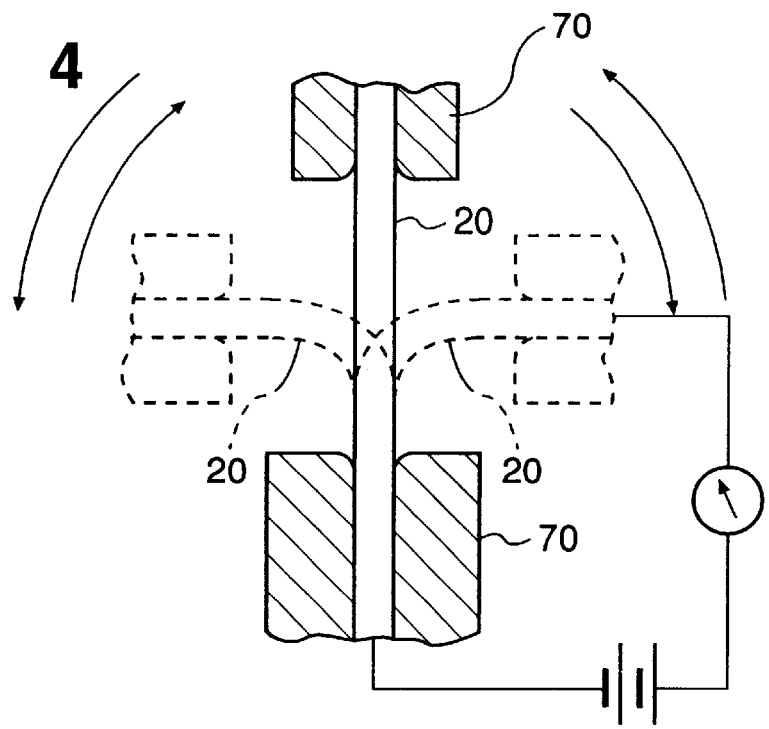
FIG. 4 is a conceptual view of a flexure test.

Samples of Examples 1 to 3 and Comparative Examples 1 to 4 were prepared, and were tested by a flexing machine shown in FIG. 4. Each sample was held in an immobile state by using a pair of upper and lower fixing metal fixtures 70 having such a shape that does not cause stress concentration. The flexure test was performed by flexing one end of each sample through 90° on each side, and a change in electrical resistance was monitored, to obtain the results of the flexure test shown in FIG. 6.

FIG. 6 shows the number of times of flexure and the number of fractured conductive coils. Referring to FIG. 6, in Comparative Examples 1 (S1) and 2 (S2), although the sheath 22 is made of a comparatively soft material, since the conductive coil 24 has a small spring index, the torsion stress of the conductive wire 26 becomes excessive, and the conductive wire 26 was disconnected at a comparatively early time.

In Comparative Examples 4 (S4) and 3 (S3), since the sheath 22 is made of a comparatively hard material, its sheath 22 buckled, and the load was concentrated on the conductive coil 24 at this portion. The conductive wire 26 was disconnected at a comparatively early time.

As described above, it was confirmed that, according to the embodiment and its examples of the present invention, excellent flexure durability was obtained. Even if small flexure occurs, because of the soft characteristics, the mechanical stress applied by the lead body onto the body tissue can be reduced.

The present invention includes any arrangements that can be selected in order to obtain substantially the same effect as that described in this specification, as a matter of course.

As has been described above, according to the present invention, there is provided an implantable electrode lead in which durability against the pressure applied under the clavicle, repeated flexure caused in the body tissue, or flexure with a very small radius of curvature is improved, and the lead body has softness, so that the mechanical stress applied by the lead body on the body tissue can be reduced.

What is claimed is:

1. An implantable electrode lead comprising:
    a lead body having a proximal end and a distal end;
    an implantable device;
    connecting means arranged at the proximal end of the lead body and mechanically and electrically connected to the implantable device;
    at least one electrode arranged at the distal end of said lead body to transmit an electrical signal between said implantable device and said electrode when implanted in a predetermined portion to perform one or both of transmission of electrical stimulation to body tissue and sensing of an electrical signal from the body tissue;
    said lead body comprising
        a conductive coil obtained by helically winding a plurality of conductive wires each formed with an insulating coating layer and having a diameter (d), each said conductive wire is formed of a first metal material having low electric resistivity and a second metal material having excellent corrosion resistance and mechanical characteristics to form a cladding, the conductive coil being a multi-filar structure having an outer surface and a coil pitch diameter (D), and a sheath made of a bio-compatible electrically insulating material covering the outer surface of said conductive coil, the sheath having an inner surface; and said lead body having an outer diameter of not more than 2 mm, said electrically insulating material of said sheath is formed of a soft material having a Shore hardness of less than 80A, said conductive coil has a spring index (D/d) greater than 7.8, and a clearance between the outer surface of the conductive coil and the inner surface of the sheath is not less than 50 $\mu$m to provide a number of times of flexure of more than $10^8$.

2. The lead according to claim 1, wherein the at least one electrode comprises:

a plurality of electrodes so that one of said conductive wires can transmit one electrical signal while others of the plurality of said conductive wires can transmit other electrical signals.

3. The lead according to claim 1, wherein the conductive wire comprises a plurality of conductive wires to transmit one electrical signal.

4. The lead according to claim 1, wherein said insulating coating layer of said conductive coil is formed of a fluoroplastic material.

5. The lead according to claim 1, wherein the first metal material is a material having an electric resistivity of not more than 5.0 $\mu\Omega$·cm at a temperature of 20° C.

6. The lead according to claim 1, wherein the first metal material is silver.

* * * * *